United States Patent
Pak et al.

(10) Patent No.: US 6,878,688 B2
(45) Date of Patent: Apr. 12, 2005

(54) METHOD OF TREATMENT OF MALIGNANT NEOPLASMS AND COMPLEX PREPARATION HAVING ANTINEOPLASTIC ACTIVITY FOR USE IN SUCH TREATMENT

(75) Inventors: Vladimir Nikolaevich Pak, Novosibirsk (RU); Natalia Anatolievna Pak, Novosibirsk (RU); Sergei Stepanovich Reshetnikov, Novosibirsk (RU); Sergei Danilovich Nikonov, Novosibirsk (RU); Anatoli Pavlovich Ogirenko, Novosibirsk (RU)

(73) Assignee: Celecure AS, Tallinn (EE)

( * ) Notice: Subject to any disclaimer, the term of this patent is extended or adjusted under 35 U.S.C. 154(b) by 0 days.

(21) Appl. No.: 09/885,645

(22) Filed: Jun. 20, 2001

(65) Prior Publication Data

US 2002/0051778 A1 May 2, 2002

(30) Foreign Application Priority Data

Jun. 22, 2000 (RU) ........................................ 2000116417

(51) Int. Cl.⁷ .............................................. A61K 38/00
(52) U.S. Cl. ........................................................ 514/12
(58) Field of Search ........................................... 514/12

(56) References Cited

FOREIGN PATENT DOCUMENTS

| RU | 2026688 C1 | 1/1995 |
| RU | 2058153 C1 | 4/1996 |
| RU | 2065307 | 8/1996 |
| RU | 2071351 | 1/1997 |

OTHER PUBLICATIONS

Gura (Science, 1997, 278:1041–4042).*
Goodman and Gilman, 6th Ed., 1980, MacMillan Publishing Co., NY, p. 861 and p. 1232.*

PubMed abstract PMID:8673023 of Severin, et al., "Alpha–fetoprotein–mediated targeting of anti–cancer drugs to tumor cells in vitro", *Biochem Mol Biol Int*. Oct. 1995; 37(2):385–92.

PubMed abstract PMID:10439917 of Severin, et al., "Antitumor activity of a covalent conjugate of the endiene antibiotic esperamicin A1 with human alpha–fetoprotein", *Dokl Akad Nauk*. Jun. 1999; 366(4):561–4.

Russian Agency for Patents and Trademarks abstracts of RU 2 1 34589 published Aug. 20, 1999, "Method of Treatment of Patients with Primary Liver Cancer and Set for Treatment of Patients with Primary Liver Cancer".

Russian Agency for Patents and Trademarks abstract of RU 2179452 published Feb. 20, 2002, "Method to Treat Malignant Neoplasms and Combined Preparation of Antitumor Action to Perform the Method".

\* cited by examiner

*Primary Examiner*—Susan Ungar
(74) *Attorney, Agent, or Firm*—Ladas & Parry LLP

(57) ABSTRACT

The present invention relates to a method of treatment of malignant neoplasms and to a complex preparation having antineoplastic activity for use in such treatment. The complex preparation comprises alpha-fetoprotein (AFP), a polyene antibiotic, mainly amphotericin B or nystatin, and a saccharide filler, mainly glucose or dextran 40, dextran 70 and dextran 100, wherein a mass ratio of the AFP to the polyene antibiotic to the saccharide filler is 1:(60–100):(50–70). The method of treatment comprises parenteral injection to a patient in need of such treatment with the said complex preparation in a course of 10 injections once in three days.

5 Claims, No Drawings

METHOD OF TREATMENT OF MALIGNANT NEOPLASMS AND COMPLEX PREPARATION HAVING ANTINEOPLASTIC ACTIVITY FOR USE IN SUCH TREATMENT

The invention relates to the field of medicine, oncology in particular, and can be used for chemotherapeutical treatment of oncological patients, suffering from different kinds of malignant neoplasms.

Methods of treatment of cancer by means of chemical preparations are known. According to mechanism of action chemical preparations are subdivided into alkylating agents, antimetabolites, alkaloids, antibiotics, hormones, immunomodulators and some others. In the course of treatment by different chemical preparations, the advantages and disadvantages thereof have been revealed.

Owing to comparatively small working concentrations, the chemical preparations affecting DNA are widely used. Alkylation of the vital DNA molecule leads to incapability of normal fission of cells and to their subsequent elimination. However, at the same time, DNA of normal non-cancerous cells is also subjected to alkylation. In order to reduce toxicity in relation to normal cells, when such preparations are applied, the methods for targeted delivery of preparations to cancerous cells by means of specific ligands, for example alpha-fetoprotein (AFP), are used. AFP is a transport protein, capable of delivering the substance bounded thereto to the cells having corresponding receptors. Such receptors abound on actively proliferating cancerous cells.

The method of treatment of primary liver cancer by means of intra-arterial injection of AFP in an amount of 2–20 mg, mainly 15 mg, five times at an interval of 7–12 days is known (Patent RU No. 2,058,153, cl. A 61 K 38/00, published Apr. 20, 1996, Bulletin No. 11).

The known method foresees the use of large amounts of AFP and distinguishes by long duration and limited extent of use, since the conditions for selecting patients for treatment by such a method are absence of jaundice and ascites, unoperability, absence of serious concurrent diseases.

The method of treatment of malignant neoplasms by means of intravenous injection of a complex preparation, comprising AFP and estrone-doxorubicin conjugate (Patent RU No. 2,026,688, cl. A 61 K 38/00, published Jan. 20, 1995, Bulletin No. 2), is known. For preparation of the complex preparation impure AFP, an abortive material is used which is concentrated after rough purification to the content of AFP of 100 μg/ml and is then sterilized. Thereafter an antineoplastic antibiotic—doxorubicin is subjected to conjugation with a ligand—estrone in an equimolar ratio. Immediately 1–2 hours before intravenous injection the concentrate of AFP in an amount of 100 ml is mixed with 20 ml of the conjugate and thus one dose of the complex preparation for one injection (a single dose of AFP comprises 10 mg) is obtained. The overall course of treatment comprises 6 injections (three times every other day at an interval of a week).

The disadvantage of the known method is the use of high doses of AFP, the disadvantage of the known complex preparation is a labour-intensive procedure of obtaining the triple complex AFP-estrone-doxorubicin and impossibility of storage of the preparation for more than 2 hours.

The closest method to the present method—the prototype—is a method of treatment of primary liver cancer, comprising injection of the preparation doxorubicin dissolved in Lipiodol ultrafluid into the liver artery, while as the preparation doxorubicin doxorubicin-estrone dissolved in 96% ethyl alcohol at 70–76° C. in a dose of 20–60 mg in 10–15 ml of Lipiodol ultrafluid is used. 20 minutes prior to that a dose of 2–10 mg of AFP in 12–15 ml of physiological salt is injected into the liver artery; the repeated treatment is carried out after 3–4 weeks (U.S. Pat. No. 2,065,307, cl. A 61 K 38/17, published Aug. 20, 1996, Bulletin No. 23).

The disadvantages of the known method are:
labour-intensity of the method, connected with separated injection of AFP and of doxorubicin-estrone complex;
the use of high concentrations of the chemical preparations (AFP—2–10 mg, doxorubicin-estrone complex—20–60 mg), which can lead to toxic side reactions;
high cost of treatment.

The closest complex preparation to the present complex preparation—the prototype—is a kit used for treatment of primary liver cancer and comprising doxorubicinestrone in an amount of 20–60 mg in 15 ml vials, Lipiodol ultrafluid in two ampules by 10 ml, AFP in an amount of 2–10 mg in 10 ml vials, physiological salt in volume of 15 ml in an ampule and 96% ethyl alcohol in volume of 5 ml in am ampule Patent Ru 2,065,307, cl. A 61 K 38/17, published Aug. 20, 1996, Bulletin No. 23).

The disadvantages of the known kit are:
labour-intensity and duration of obtaining the sterile doxorubicin-estrone complex as well as labour-intensity of preparation of the working solution of the given preparation: the preparation is dissolved in 0.5–1.5 ml of 96% ethyl alcohol, heating to 70–76° C., the resultant solution is transferred into 10–15 ml of previously upwarmed Lipiodol ultrafluid, the suspension thus obtained is cooled to 32–37° C. and is then injected into the liver artery under X-ray television control;
high concentrations of the preparations used in the kit;
polycomponent nature of the kit.

The technical object of the group of the inventions is to simplify the known method, to lower the doses of the preparations to be injected and to reduce the costs of treatment.

The established object has been achieved by means of hereby proposed method of treatment of malignant neoplasms and a complex preparation having antineoplastic activity for use in such treatment.

The realization of the method of treatment.

Depending on the character and seriousness of the disease, to a patient, together with the basic infusion-detoxication therapy, the complex preparation, comprising AFP in an amount of 0.07–0.15 mg, a polyene antibiotic in an amount of 4.2–7.0 mg and a pharmaceutically suitable filler, is parenterally injected once within twenty-four hours at an interval of three days in a course of 10 infusions.

The complex preparation having antineoplastic activity comprises the following components, in mg:

| | |
|---|---|
| AFP | 0.07–0.15 |
| a polyene antibiotic | 4.2–7.0 |
| a filler | 3.5–5.0 |

As a polyene antibiotic amphotericin B or nystatin is mainly used.

As a filler sugars are mainly used, for example glucose or synthetic polymers, selected from the group of polysaccharides, for example polyglucin, rheopolyglucin and dextran 100.

The complex preparation is obtained as follows: AFP with purity not less than 98% is dissolved in distilled water or physiological salt in an amount of 0.07–0.15 mg/ml, whereto a polyene antibiotic in an amount of 4.2–7.0 mg/ml and then a filler in an amount of 3.5–5.0 mg/ml are added, after that the components are carefully mixed and the resultant mixture is then left to stand at 18–25° C. for 10–12 hours. Thereafter the solution is sterilized by filtration, pre-packed in ampules or vials having a capacity of 1.2 or 3 ml and freeze-dried. The mass ratio of AFP, a polyene antibiotic and a filler is 1:(28–100):(23–71).

The complex preparation (conventional designation Reducin) is a powder of yellow colour, soluble in water, in physiological salt, in glucose solution and in other diluents (carriers), suitable for intravenous injection. One ampule of the complex preparation comprises: 0.07–0.15 mg of AFP, 4.2–7.0 mg of polyene antibiotic and 3.5–5.0 mg of corresponding filler. For preparation of the working solution the content of the ampule is dissolved in 2–3 ml of sterile water and is then transferred into 200 ml vial together with a carrier, suitable for intravenous injection.

The present method comprises injection to a patient of a new complex chemical preparation having antineoplastic activity and consisting of a vector part (AFP), specific to cancerous cells, and a nonspecific part, comprising a cytotoxic substance. As the latter an essentially new channel-forming and surface-active agent (SAA), namely a polyene antibiotic, for example amphotericin B or nystatin, which have not been previously used as antineoplastic remedies, is used. The targets for the new complex preparation are membranes of intracellular substructures. Such substructures include mitochondria, lysosomes, endoplasmatic reticula (EPR), nuclei, etc. In case of disorders in the function of membranes of substructures, a normal cell function, ensurable by the compartmentalization of different functions, is impossible. As a result autodigestion of cancerous cells takes place according to the mechanism of induced apoptosis.

The use of AFP as a vector for targeted delivery of cytotoxic preparations to cancerous cells is known (see for instance patent RU No. 2,071,351, cl. A61 K 38/17, published Jan. 10, 1997). In all known cases AFP is bounded with a cytotoxic part of the preparation by a chemical covalent bond, whereas in the present complex preparation AFP and SAA form a noncovalent complex, ensuring simultaneously the stability of the macromolecule during transportation and its functional independence in the process of cytotoxic action of the polyene antibiotic. The activity of the present complex preparation is based on the initiation of physiological reduction of cancerous cells according to the mechanism similar to that of apoptosis. As a rule, the natural autodestruction of the cells of tumor under the influence of the present complex preparation does not lead to intoxication of the organism and the effect of the treatment appears quickly.

The essential distinctive features of the present method, as compared with those of the prototype, are:
  to a patient the complex preparation, comprising AFP in an amount of 0.07–0.15 mg, a polyene antibiotic in an amount of 4.2–7.0 mg and a pharmaceutically suitable filler, is injected parenterally and simultaneously in a course of 10 injections (infusions) once in three days, which enables to simplify the known method, to lower the doses of the preparations to be injected and to reduce the costs of treatment.

The essential distinctive features of the present complex preparation, as compared with those of the known preparation, are:
  the complex preparation comprises additionally a surface-active agent, namely a polyene antibiotic, mainly amphotericin B or nystatin, in an amount of 4.2–7.0 mg, which provides the complex with a new type of bond with a vector part—with a noncovalent bond, and a new mechanism of interaction with cancerous cells—with the membranes of the substructures of cancerous cells (membranes of lysosomes, EPR, mitochondria, nuclei), which, in its turn, improves the efficiency of the treatment and reduces side complications;
  the complex preparation comprises the components in optimal, experimentally selected amounts and ratios, namely: AFP—0.07–0.15 mg, a polyene antibiotic—4.2–7.0 mg, a filler—3.5–5.0 mg, which enables to improve the efficiency of the treatment and substantially lower the doses of the active components used.

Being supported by the fact that no analogous method of treatment of malignant neoplasms and no analogous complex preparation having antineoplastic activity have been revealed, it may be concluded that the present group of inventions meet the requirements for patentability in respect of "novelty" and "inventive step".

The present method has been tested on 8 patients having IV clinical stage of oncological diseases, progressing after traditional ways of treatment. A full or a partial clinical effect has been achieved on 6 patients out of 8 (75%). The terms of remission were from 6 months to 1.5 years. In majority cases, for achieving a well-defined clinical effect it was sufficient to conduct one course of treatment.

The inventions are characterized by the following Examples.

EXAMPLE 1

For preparation of the complex preparation Reducin 700 mg of AFP, 42 g of amphotericin B and 50 g of rheopolyglucin are dissolved in 1 litre of distilled water by mixing, subsequently the volume is increased up to 10 litres. The resultant mixture is incubated at room temperature for 10–12 hours and is then subjected to sterilization by filtration through a membrane filter, pre-packed in 10,000 ampules or vials by 1 ml (a single dose) and thereafter freeze-dried in aseptic conditions. One ampule (vial) comprises 0.07 mg of AFP, 4.2 mg of amphotericin B and 5.0 mg of rheopolyglucin.

EXAMPLE 2

The complex preparation Reducin is obtained analogously to Example 1, with the exception that to water solution 1 g of AFP, 50 g of amphotericin B and 40 g of polyglucin are added. As a result the preparation, comprising 0.1 mg of AFP, 5.0 mg of amphotericin B and 4.0 mg of polyglucin in a single dose, is obtained.

EXAMPLE 3

The complex preparation is obtained analogously to Example 1, with the exception that to water solution 1.5 g of AFP, 70 g of amphotericin B and 30 g of dextran (molecular mass 100 kDa, Serva) are added. As a result the preparation, comprising 0.15 mg of AFP, 7.0 mg of amphotericin B and 3.0 mg of dextran in a single dose, is obtained.

EXAMPLE 4

The complex preparation is obtained analogously to Example 1, with the exception that to water solution 750 mg of AFP, 60 g of nystatin and 50 g of glucose are added. As a result the preparation, comprising 0.075 mg of AFP, 6.0 mg of nystatin and 5.0 mg of glucose in a single dose, is obtained.

EXAMPLE 5

Patient L., 54 years old, the patient record No. 587, was hospitalized on Apr. 02, 1999 with the diagnosis: central cancer of the right lung IV stage (recidivation, progressive course), cancer of the left mammary gland II stage (remission). The patient was complaining weakness, dyspnea, exhausting cough.

The data of the inspection. X-ray photograph of the organs of thorax: on both sides in the lungs there are numerous polymorphous shadows of metastases in sizes from 0.5 to 2.5 cm and of medium intensity and uneven outlines. The shadow of mediastinum has shifted rightwards and expanded. The right lung field has diminished in volume; below the fourth rib there is an intensive overshadowing because of the liquid in the pleural cavity.

A course of polychemotherapy was conducted according to the scheme CAF: On the $1^{st}$ and $8^{th}$ days intravenously 1 g of cyclophosphane, on the $1^{st}$ and $8^{th}$ days intravenously 500 mg of 5-fluorouracil, on the $2^{nd}$ and $9^{th}$ days of the treatment intravenously 40 mg of adriablastin. The treatment was accompanied by high toxicity without an expressed clinical effect.

Thereafter the patient was treated according to the present method. The complex preparation Reducin, comprising 0.07 mg of AFP, 4.5 mg of amphotericin B and 5.0 mg of glucose, was injected by infusion in a course of 10 injections once in three days. The condition of the patient has improved and became satisfactory a week after the course of treatment had been finished. On the basis of the data of the radiology inspection of the organs of thorax favourable changes were registered, characterized by the decreased number of metastases in the lungs and the weakening of intensity of the shadows of dissemination. The liquid in the pleural cavity was not inspected. Dyspnea on ascent has diminished and cough disappeared completely. During the treatment with Reducin a rise in temperature and a shiver were observed, which were treated with standard preparations.

EXAMPLE 6

Patient M., 62 years old, the patient record No. 800, was hospitalized with the diagnosis: central cancer of the right lung IV stage (adenocarcinoma); spread metastases in head, in the right hemisphere of brain, in neck, in thorax; right-sided carcinomatous pleurisy; chronic deforming bronchitis; pulmonary emphysema; diabetes of the 2nd type; IBO; angina of efford; secondary immunodeficiency, undernourishment, condition after the courses of polychemotherapy.

The treatment program included a course of polychemotherapy according to the scheme CAMF. To the patient were injected 1 g of cyclophosphane on the $1^{st}$ and $8^{th}$ days, adriamicin on the $1^{st}$ and $8^{th}$ days, 50 mg of methotrexate on the $1^{st}$ and $8^{th}$ days, 5-fluorouracil on the $2^{nd}$ and $9^{th}$ days. The treatment was accompanied by endotoxicosis and an abrupt worsening of the condition of the patient. No positive effects were detected.

Because of complicated condition of the patient, to him intravenous infusions of the complex preparation Reducin, comprising 0.075 mg of AFP, 5.0 mg of nystatin and 5.0 mg of rheopolyglucin in a single dose, in a course of 10 infusions once in three days were prescribed.

6 days after the beginning of the treatment according to the present method the diminishing of the sizes of subcutaneous metastases were noted. By the end of the treatment rapid improvement of the main disease was noted, which became apparent from the twofold reduction of the size of all surface metastatic nodes, the disappearing of pains in the lower jaw, the decreasing of the rate of exudation in the right pleural cavity. Thrice conducted right-sided pleural punction proved the decreasing of volume of exudate: before the treatment the volume of exudate was 600 ml, a week after the treatment—350 ml, three weeks after the treatment—20 ml. The improvement of function of central nervous system became apparent from restoration of normal swallowing function, restoration of gripping function of the left hand, clinically corresponding to the reduction of metastasis in the right hemisphere of brain.

The use of the present method of treatment of malignant neoplasms and the complex preparation having antineoplastic activity, as compared with the known method of treatment and the kit for use in such treatment, enables:

to simplify the method of treatment by means of simultaneous parenteral injection of the complex preparation, comprising AFP and cytotoxic SAA in optimal ratios;

to lower the doses of the used components: AFP 13–140 times, the cytotoxic component 3–14 times;

to improve the efficiency of treatment by means of using the complex preparation having high specifity to growing cancerous cells and optimal composition of the complex preparation having a long term of storage (two years);

to reduce the costs of treatment by means of using a small number of components in the complex preparation and low doses of the chemical preparations to be used.

Thus, while using the present method of treatment of malignant neoplasms two biological mechanisms are realized. The first of them comprises the targeted delivery of the cytotoxic agent by means of AFP to tumorous cells. The second one comprises the directed destruction of the tumorous cells because of destruction of the intracellular structures, in particular EPR and lysosomes. This may be accompanied by autodigestion of tumorous cells, caused by the enzymes of hydrolysis, comprising in the lysosomes, according to the mechanism of targetably induced apoptosis. The directed reduction affects much less the cells of blood-forming, immune and other constantly growing systems, being often damaged when standard antineoplastic chemotherapy is applied. The present complex preparation Reducin distinguishes by high efficiency of antineoplastic activity, a small number of components, simplicity of preparation and a long term of storage.

What is claimed is:

1. A method for treatment of a malignant neoplasm, expressing alpha-fetoprotein receptor (AFPR), the method comprising injecting complex preparation comprising alpha-fetoprotein (AFP), amphotericin B or nystatin, and a polysaccharide filler or glucose, wherein the mass ratio of the AFP to amphotericin B or nystatin to the polysaccharide filler or glucose is 1:(28–100):(23–71).

2. A complex preparation for treatment of a malignant neoplasm, expressing alpha-fetoprotein receptor (AFPR), comprising alpha-fetoprotein (AFP), amphotericin B or nystatin, and a polysaccharide filler or glucose, wherein the mass ratio of the AFP to amphotericin B or nystatin to the polysaccharide filler or glucose is 1:(28–100):(23–71).

3. The complex preparation of claim 2, wherein the polysaccharide filler is selected from the group consisting of polyglucin, rheopolyglucin and dextran 100.

4. The method of claim 1, wherein the polysaccharide filler is selected from the group consisting of polyglucin, rheopolyglucin and dextran 100.

5. The method of claim 1, further comprising injecting the complex preparation in a course of ten injections wherein an injection is administered every three days, wherein a single dose comprises 0.07–0.15 mg of the AFP, 4.2–7.0 mg of amphotericin B or nystatin, and 3.5–5.0 mg of the polysaccharide filler or glucose.

* * * * *